United States Patent
Ernst et al.

(10) Patent No.: US 7,378,558 B2
(45) Date of Patent: May 27, 2008

(54) METHOD FOR PRODUCING CAROTENOIDS

(75) Inventors: Hansgeorg Ernst, Speyer (DE); Klaus Henrich, Haβloch (DE); Andreas Keller, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 586 days.

(21) Appl. No.: 10/532,207

(22) PCT Filed: Nov. 17, 2003

(86) PCT No.: PCT/EP03/12804

§ 371 (c)(1),
(2), (4) Date: Apr. 22, 2005

(87) PCT Pub. No.: WO2004/048323

PCT Pub. Date: Jun. 10, 2004

(65) Prior Publication Data

US 2006/0106257 A1 May 18, 2006

(30) Foreign Application Priority Data

Nov. 22, 2002 (DE) ............................. 102 54 809

(51) Int. Cl.
*C07C 45/68* (2006.01)
*C07C 49/543* (2006.01)
*C07C 43/03* (2006.01)
*C07C 35/18* (2006.01)
*C07C 69/73* (2006.01)

(52) U.S. Cl. ................ 568/343; 568/378; 568/673; 568/824; 560/183

(58) Field of Classification Search ................ None
See application file for complete search history.

(56) References Cited

U.S. PATENT DOCUMENTS

| 5,455,362 | A | * | 10/1995 | Ernst et al. | ................ 549/437 |
| 5,654,488 | A | * | 8/1997 | Krause et al. | ............... 568/345 |
| 6,150,561 | A | * | 11/2000 | Kreienbuhl et al. | ......... 568/352 |
| 6,743,954 | B2 | * | 6/2004 | Ernst et al. | ................ 568/824 |
| 6,747,177 | B2 | * | 6/2004 | Ernst et al. | ................ 568/828 |

FOREIGN PATENT DOCUMENTS

EP 0 908 449 4/1999

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process for preparing carotenoids, in which the process includes reacting a dialkoxy dialdehyde in a double Wittig condensation with a phosphonium salt of or in a double Wittig-Horner condensation with a phosphonate. The carotenoids include, for example, β-carotene, zeaxanthin, canthaxanthin, astaxathin, lycopene and croceptin, which are useful as nutraceuticals, food colorants, and feed additives.

7 Claims, No Drawings

METHOD FOR PRODUCING CAROTENOIDS

The invention relates to a process for preparing carotenoids, for example β-carotene, zeaxanthin, canthaxanthin, astaxanthin, lycopene and crocetin, which are in demand as nutraceuticals, food colorants and feed additives.

It is known that carotenoids are prepared inter alia by double Wittig condensation of a $C_{15}$ phosphonium salt ($C_{15}$—P) with a symmetrical $C_{10}$ dialdehyde (Carotenoids, Vol. 2, page 89 et seq., Birkhäuser Verlag, 1996).

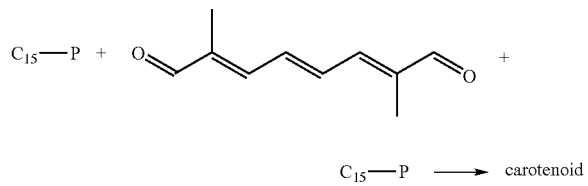

Depending on the structure of the carotenoid to be prepared, it is possible for example to react the following $C_{15}$ phosphonium salts (P1 to P5) in the abovementioned Wittig reaction, where Ph is a phenyl radical and $X^-$ is the anion equivalent of an inorganic or organic acid:

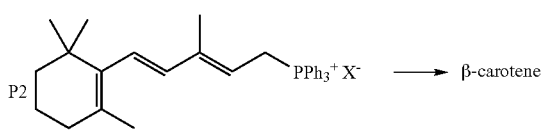

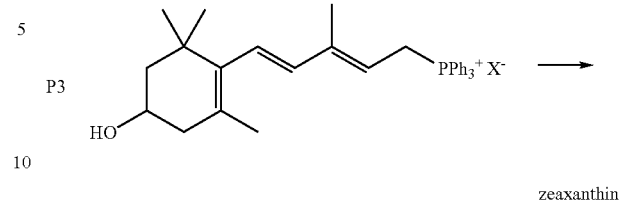

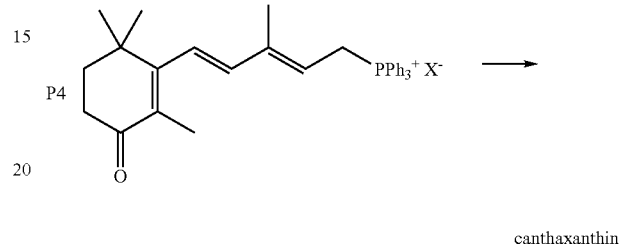

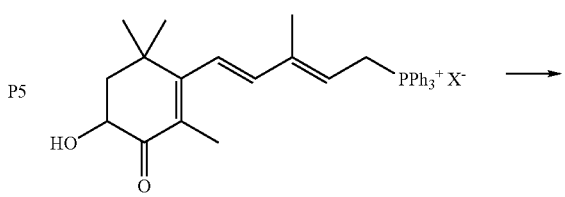

For the synthesis of crocetin diesters as precursors of the saffron pigment crocetin, $C_5$ ester phosphonium salts ($C_5$—P) or $C_5$ ester phosphonates ($C_5$-EP) under respectively Wittig or Wittig-Horner condensation with the $C_{10}$ dialdehyde (Angew. Chem. 72, 911 (1960); Chem. Ber. 93, 1349 (1960)).

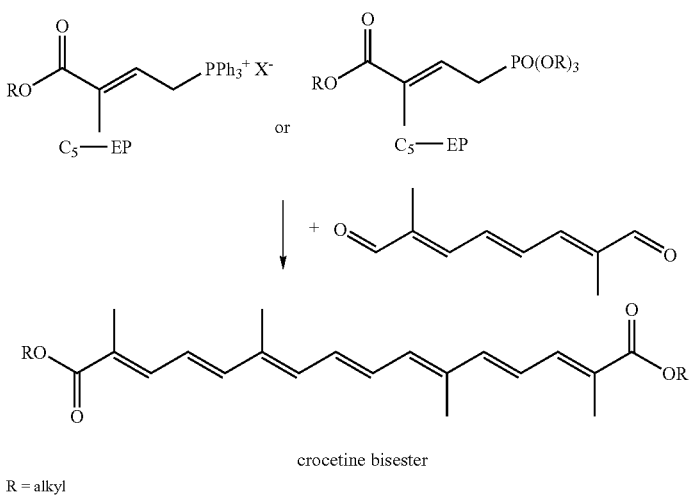

R = alkyl

The $C_{10}$ dialdehyde required for these synthetic processes is a crystalline substance which is only slightly soluble in many solvents. Carotenoid syntheses using $C_{10}$ dialdehyde must therefore usually be carried out in chlorinated hydrocarbons such as dichloromethane or trichloromethane or in oxiranes as solvents or co-solvents (Carotenoids, Vol. 2, pages 92 et seq.; Birkhäuser-Verlag, 1996). The use of such solvents for preparing food additives is objectionable from the toxicological viewpoint.

This is why various processes have been proposed, inter alia in EP-A-0 733 619 and EP-A-0 908 449, for carrying out these industrial processes in toxicologically less objectionable solvents such as, for example, lower alcohols. However, all these processes still require the preparation and isolation, and handling and metering, of the crystalline $C_{10}$ dialdehyde. Handling of solids is, however, associated with high capital costs and thus high production costs.

One possibility for avoiding this disadvantage is disclosed in EP-A-0 509 273.

The process described therein employs 2,5-dihydrofuran of the formula (1), which is in the form of an oil and which is prepared by reacting a 2,5-dialkoxy-2,5-dihydrofuran (2) with an alkyl propenyl ether (3), as synthetic equivalent for the $C_{10}$ dialdehyde.

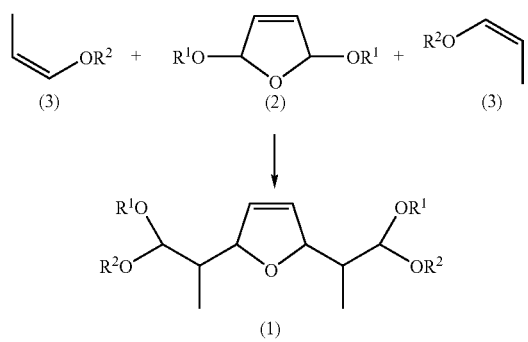

However, this process has the following disadvantages. The stated yields of (1) are from 38 to 56% of theory, which is insufficient for industrial implementation. Other publications confirm that analogous processes generally give only low yields of bisalkylation product (1) (J. Gen. Chem. USSR, 32, 4, 1082 f. (1962); Tetrahedron Lett. 42, 10, 2003 f. (2001)). The only example indicated of a carotenoid synthesis was the reaction of (1) to give β-carotene in an overall yield of 52%. This process is industrially and economically unattractive because the availability of (1) is poor and the yield is low.

It was therefore an object of the present invention to provide a process for preparing carotenoids which does not have the disadvantages of the prior art described at the outset.

This object has been achieved by a process for preparing carotenoids which comprises reacting a dialkoxy dialdehyde of the general formula I

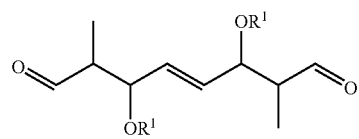

with $R^1$=$C_1$-$C_6$-alkyl, in a double Wittig condensation with a phosphonium salt of the formula II or in a double Wittig-Horner condensation with a phosphonate of the formula III

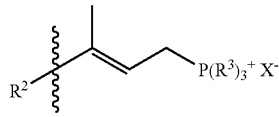

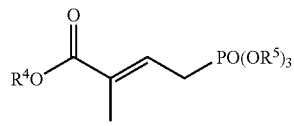

in which the substituents have independently of one another the following meaning:

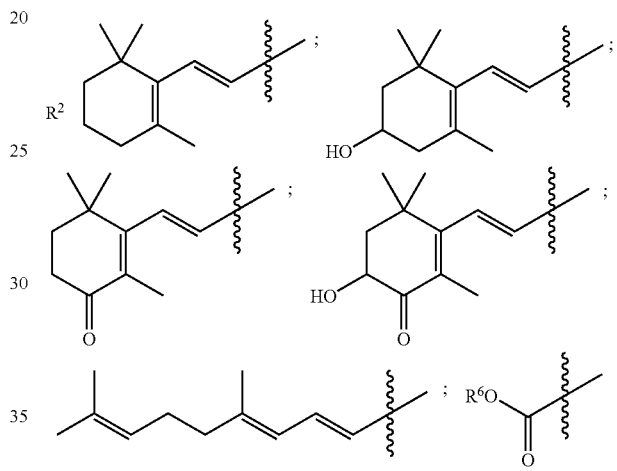

$R^3$ aryl;
$R^4$ to $R^6$
  $C_1$-$C_6$-alkyl and
$X^-$ an anion equivalent of an inorganic or organic acid.
Alkyl radicals which may be mentioned for $R^1$ and $R^4$ to $R^6$ are branched or unbranched $C_1$-$C_6$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. Preferred alkyl radicals are $C_1$-$C_4$-alkyl groups, particularly preferably methyl, ethyl, n-propyl and 1-methylethyl, very particularly preferably methyl and ethyl.

The term aryl for $R^3$ refers to conventional aryl radicals occurring in phosphines and phosphonium salts, such as phenyl, tolyl, naphthyl, optionally substituted in each case, preferably phenyl.

The radical $X^-$ is an anion equivalent of inorganic or organic acid, preferably a strong inorganic or organic acid.

The term strong acid comprises hydrohalic acids (especially hydrochloric acid and hydrobromic acid), sulfuric acid, phosphoric acid, sulfonic acids and other inorganic or organic acids with a comparable degree of dissociation. Strong organic acids also mean in this connection $C_1$-$C_6$-alkanoic acids.

Anions which should be particularly preferably mentioned are those of an acid selected from the group consisting of hydrochloric acid, hydrobromic acid, sulfuric acid, phosphoric acid, formic acid, acetic acid and sulfonic acids. Very particular preference is given to $Cl^-$, $Br^-$, $C_nH_{2n+1}$—$SO_3^-$ (with n=1-4), $Ph$-$SO_3^-$, $p$-$Tol$-$SO_3^-$ or $CF_3$—$SO_3^-$.

A preferred embodiment of the process of the invention relates to the preparation of a carotenoid selected from the group consisting of astaxanthin, lycopene and canthaxanthin, which comprises reacting a dialkoxy dialdehyde of the formula Ia

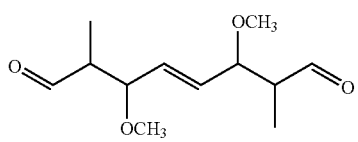

Ia with a phosphonium salt of the formula IIa,

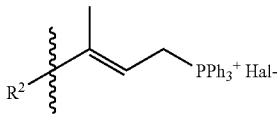

IIa in which the substituents have independently of one another the following meaning:

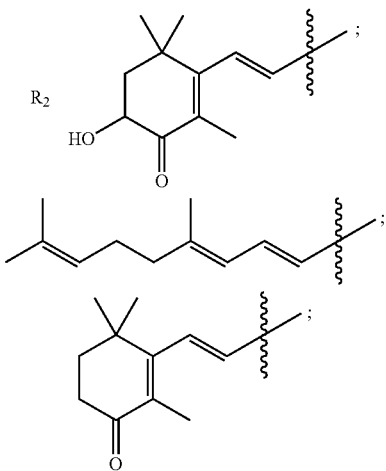

Ph phenyl;
Hal halide, preferably $Cl^-$ or $Br^-$.

The Wittig or Wittig-Horner reactions generally take place under the conditions described for these reactions (Carotenoids, Vol, 2, pages 79 et seq., Birkhäuser-Verlag, 1996, and references cited therein; and EP-A-0 733 619). The reaction can be carried out for example in a system consisting of an inert organic solvent such as, for example, chlorinated hydrocarbons or cyclic or open-chain ethers in combination with an alkali metal or alkaline earth metal alkoxide, preferably a solution in the corresponding alkanol. An alternative possibility in this case too is to employ an oxirane, preferably 1,2-epoxybutane, in a manner known per se as latent base and cosolvent in combination with a lower alkanol.

All bases customary for Wittig condensations, e.g. alkali metal hydroxides such as sodium hydroxide, potassium hydroxide or lithium hydroxide; alkali metal hydrides such as sodium hydride or potassium hydride, can be used as base.

However, it is preferred to use a solvent in which the desired final product is slightly soluble but the triphenylphosphane oxide resulting as coproduct from the Wittig reaction is readily soluble.

Suitable for this purpose are in particular lower alcohols, preferably $C_1$-$C_6$ alcohols, for example methanol, ethanol, n-propanol, isopropanol, n-butanol or tert-butanol, particularly preferably methanol. The base advantageously used in this case an alkali metal or alkaline earth metal alkoxide, preferably Na methoxide. Triphenylphosphine oxide and inorganic salts can be removed by diluting the mixture with water.

The condensation normally takes place at temperatures between −30° C. and +50° C., preferably between −20 and +30° C., particularly preferably between −10° C. and +25° C., very particularly preferably between 0° C. and +20° C.

It is possible in this connection either to introduce both starting compounds (phosphonium salt and aldehyde) into the solvent and add the base thereto, or else add the base to a solution of the phosphonium salt, and only then to add a solution of the aldehyde.

The amount of base employed is normally in the range from 0.8 to 5 mol, preferably 1 to 3 mol, per mole of the phosphonium salt II or phosphonate III employed.

Following the Wittig or Wittig-Horner reaction, the products can be thermally isomerized into the all(E) form in a known manner by heating for several hours at temperatures in the range from 70 to 120° C., preferably at the boiling point of the solvent used, and be isolated in high yield and purity by filtration.

The dialkoxy dialdehyde I or Ia used according to the invention

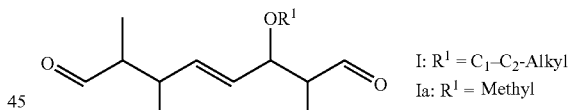

I: $R^1 = C_1$–$C_2$-Alkyl
Ia: $R^1 =$ Methyl arises as intermediate in an industrial $C_{10}$ dialdehyde synthesis starting from a hexaalkoxy derivative V, in a sequence of acetal cleavage and elimination, but is not normally isolated (Carotenoids, Vol. 2, pages 117/118 and 301/302, Birkhäuser Verlag, 1996; CH Pat. 321 106). With suitable choice of the reaction conditions, the process can be stopped at the intermediate stage of I. I can be isolated and purified by distillation (J. Gen. Chem. USSR, 34, 1, 64 f. (1964)).

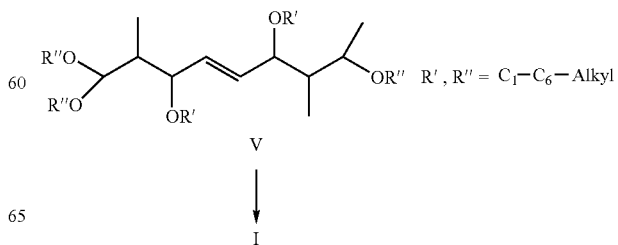

$R', R'' = C_1$–$C_6$—Alkyl

V

↓

I

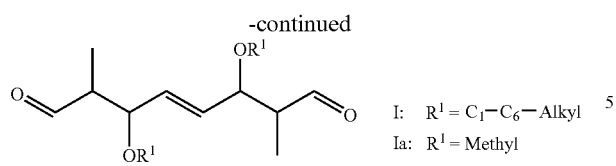

I: R$^1$ = C$_1$-C$_6$—Alkyl
Ia: R$^1$ = Methyl

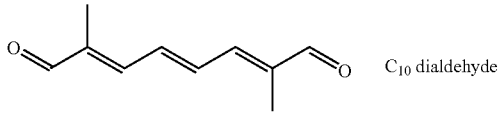

C$_{10}$ dialdehyde

The dialkoxy dialdehydes of the formula I are readily soluble, stable substances and are in the form of liquids or oils, so that the elaborate handling of C$_{10}$ dialdehyde solid is dispensed with. A further advantage of the use of I is that the process for preparing the C$_{10}$ units is shortened by one synthesis stage and one removal of solids.

It has surprisingly been found that the intermediate of the formula I, preferably Ia, is outstandingly suitable for all the abovementioned Wittig and Wittig-Horner condensations. Intermediates arising in this case are alkoxy derivatives of the general formula IV.

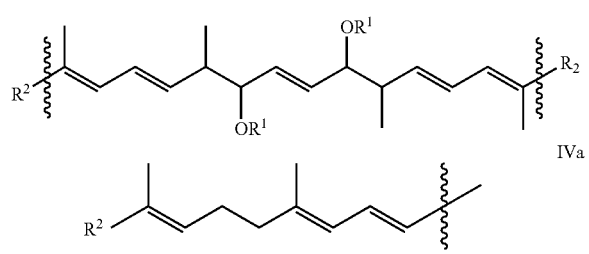

IV

IVa

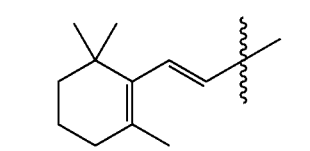

IVb

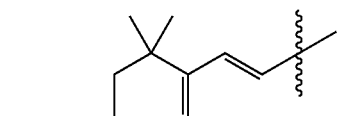

IVc

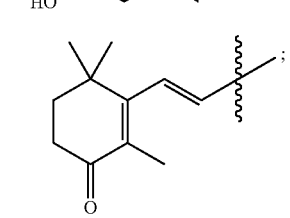

IVd

IVe

These intermediate stages can be isolated if desired. However, the elimination to the desired polyene is preferably allowed to proceed under the reaction conditions, preferably by increasing the reaction temperature.

The invention additionally relates to compounds of the formula IV

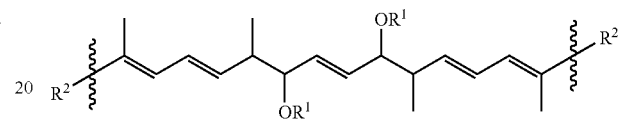

IV in which the substituents have independently of one another the following meaning:
R$^1$ C$_1$-C$_6$-alkyl;

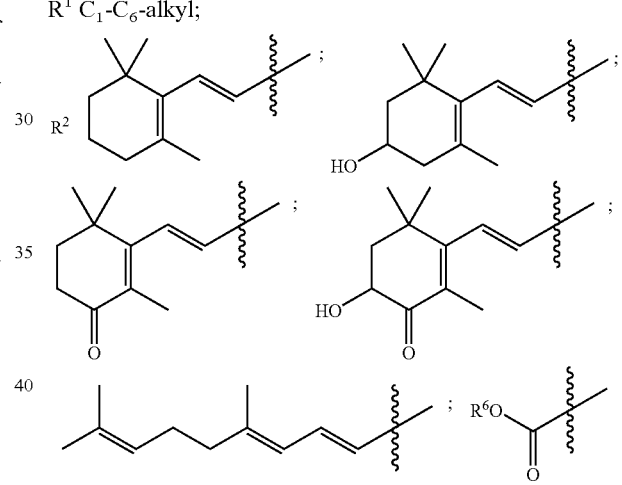

R$^6$ C$_1$-C$_6$-alkyl.

Preferred compounds are those of the formula IV

IV in which
R$^1$ is methyl or ethyl, particularly preferably methyl; and
R$^2$ is

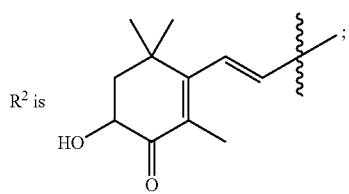

-continued

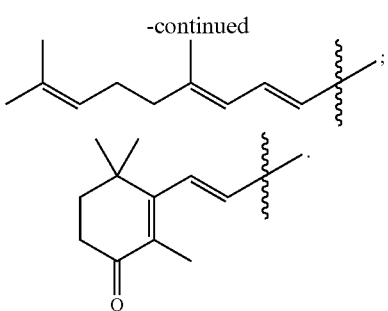

The following examples are intended to explain the process of the invention in more detail.

EXAMPLE 1

Preparation of Astaxanthin 71.9 g (0.125 mol) of astaxanthin $C_{15}$ phosphonium salt P5 ($X^-$=bromide) were introduced into 150 ml of methanol. At 0° C., 11.4 g of $C_{10}$ dial Ia (95% pure; equivalent to 0.0475 mol) were added.

Then 24.8 g of a 30% strength solution of sodium methoxide in ethanol (=0.137 mol NaOMe) were added dropwise at 0° C. over the course of 1 h, and the mixture was stirred at 0° C. for a further our and then allowed to reach room temperature. A solution of 1.5 g (25 mmol) of acetic acid in 115 ml of water was added dropwise, and the mixture was heated to reflux (about 75° C.) and then stirred under reflux for 20 h. It was allowed to reach room temperature, and the crystals were filtered off. The filter cake was washed twice with 100 ml each time of a 60:40 (v/v) methanol/water mixture, once with hot water (100 ml) and once with methanol (100 ml; 25° C.) and dried in a vacuum drying oven at +50° C.

Final weight: 23.5 g of astaxanthin=83.0% yield (based on Ia employed); HPLC purity: 99.17%

EXAMPLE 2

Isolation of the Astaxanthin Intermediate Stage IVe 71.9 g (0.125 mol) of astaxanthin $C_{15}$ phosphonium salt P5 ($X^-$=bromide) were dissolved in 250 ml of methylene chloride. At 0° C., 11.4 g of $C_{10}$ dial Ia (95% pure; equivalent to 0.0475 mol) were added. Then 46.8 g of a 20% strength solution of sodium ethoxide in ethanol (0.137 mol NaOEt) were added dropwise at 0° C. over the course of 1 h, and the mixture was stirred at 0° C. for 1 h. Then a solution of 1.5 g of acetic acid in 250 ml of water was added dropwise. The organic phase was separated off. The aqueous phase was back-extracted twice with 40 ml of methylene chloride. The combined organic phases were washed twice with 125 ml of water each time, dried over sodium sulfate and concentrated in a rotary evaporator. The bright red pasty residue was purified by flash chromatography on silica gel (eluent: cyclohexane/methyl tert-butyl ether=4:1 to 1:1).

27.05 g (86.3% of theory) of viscous red oil which, according to H-NMR, C-NMR and IR analysis, contained IVe as mixture of stereoisomers were obtained. $E^1_1$ (CHCl$_3$): 335 (260 nm); 468 (351 nm).

EXAMPLE 3

Preparation of Zeaxanthin 14.9 g (0.0288 mol) of zeaxanthin $C_{15}$ phosphonium salt P3 ($X^-$=chloride) were dissolved in 63 ml of ethanol. 2.85 g of $C_{10}$ dial Ia (95% pure; equivalent to 0.012 mol) and then 16.6 g of butylene oxide (1,2-epoxybutane) were added. The mixture was then heated under reflux for 20 h. The resulting suspension was cooled to 0° C. and stirred at this temperature for 1 h. The crystals were filtered off with suction. The filter cake was washed three times with 50 ml of ethanol each time and dried in a vacuum drying oven.

Final weight: 5.52 g of zeaxanthin=81% of theory (based on Ia employed).

We claim:

1. A process for preparing carotenoids, which comprises reacting a dialkoxy dialdehyde of the general formula I

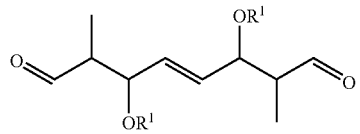

I wherein $R^1$ is $C_1$-$C_6$-alkyl, in a double Wittig condensation with a phosphonium salt of the formula II or in a double Wittig-Horner condensation with a phosphonate of the formula III

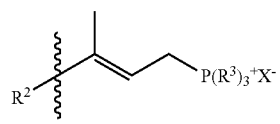

II

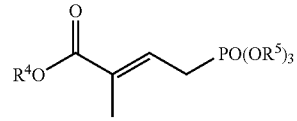

III wherein the substituents in formulas II and III, independently of one another, are defined as follows:
$R^2$ is

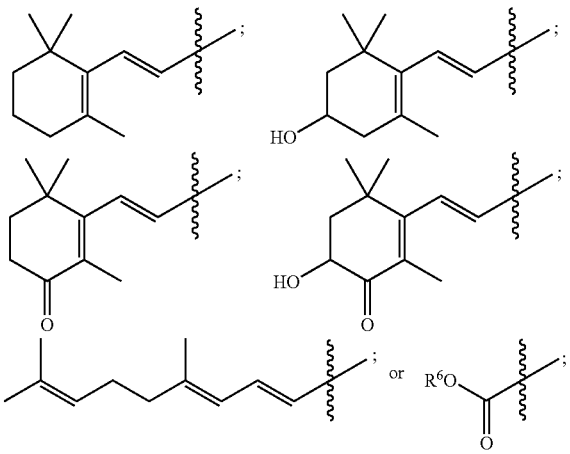

$R^3$ is aryl;
$R^4$ to $R^6$ are $C_1$-$C_6$-alkyl; and
$X^-$ is an anion equivalent of an inorganic or organic acid.

2. The process according to claim 1, wherein $X^-$ is the anion equivalent of an acid selected from the group consisting of hydrohalic acid, sulfuric acid, phosphoric acid, formic acid, acetic acid and sulfonic acid.

3. The process according to claim 2, wherein X⁻ is Cl⁻, Br⁻, $C_nH_{2n+1}$-$SO_3^-$ with n =1-4, Ph-$SO_3^-$, p-Tol-$SO_3^-$ or $CF_3$-$SO_3^-$.

4. The process according to claim 1 for preparing a carotenoid selected from the group consisting of astaxanthin, lycopene and canthaxanthin, which comprises reacting a dialkoxy dialdehyde of the formula Ia

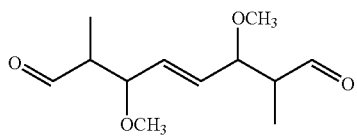
Ia with a phosphonium salt of the formula IIa,

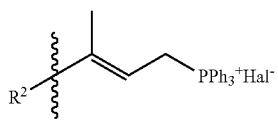
IIa in which the substituents have independently of one another the following meaning:

$R^2$ is

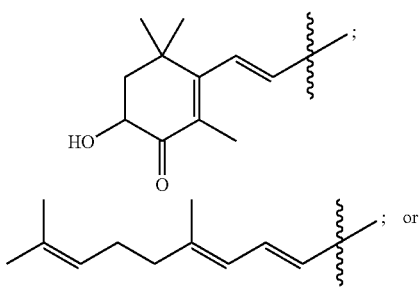

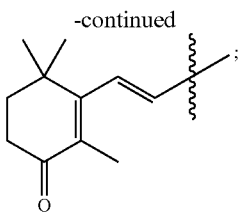

Ph is phenyl; and
Hal is halide.

5. The process according to claim 1, wherein the reaction is carried out in a $C_1$-$C_6$ alcohol using an alkali metal or alkaline earth metal alkoxide as base.

6. The process according to claim 1, wherein the reaction product is thermally isomerized into the all (E) form and isolated by filtration.

7. Compounds of the formula IV,

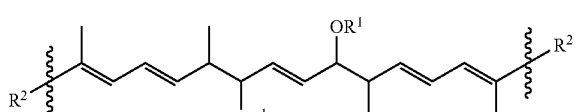
IV wherein $R^1$ and $R^2$ are independent of one another and defined in claim 1.

* * * * *